United States Patent [19]

Lakin

[11] Patent Number: 4,495,466
[45] Date of Patent: Jan. 22, 1985

[54] EDDY CURRENT TEST PROBE WITH CIRCUMFERENTIAL SEGMENTS AND METHOD OF TESTING MATERIAL SURROUNDING FASTENER HOLES

[75] Inventor: Kenneth M. Lakin, Ames, Iowa

[73] Assignee: The United States of America as represented by the Secretary of the Air Force, Washington, D.C.

[21] Appl. No.: 366,732

[22] Filed: Apr. 8, 1982

[51] Int. Cl.³ .................. G01N 27/90; G01R 33/12
[52] U.S. Cl. ..................................... 324/242; 324/207
[58] Field of Search ............... 324/200, 228, 234, 235, 324/238–243

[56] References Cited

U.S. PATENT DOCUMENTS

| | | | |
|---|---|---|---|
| 1,893,074 | 1/1933 | Drake | 324/242 |
| 2,467,306 | 4/1949 | Habig | 324/242 |
| 3,109,139 | 10/1963 | Branker | 324/240 |
| 3,166,710 | 1/1965 | Schmidt | 324/242 |
| 3,193,784 | 7/1965 | Lautzenhiser | 324/207 |
| 3,197,693 | 7/1965 | Libby | 324/233 X |
| 3,359,495 | 12/1967 | McMaster et al. | 324/235 |
| 3,449,664 | 6/1969 | Smith | 324/235 |
| 3,535,625 | 10/1970 | Pratt | 324/233 |
| 4,095,181 | 6/1978 | Harris et al. | 324/238 |
| 4,204,159 | 5/1980 | Sarian et al. | 324/232 |

FOREIGN PATENT DOCUMENTS

| | | | |
|---|---|---|---|
| 856485 | 11/1952 | Fed. Rep. of Germany | 324/228 |
| 24613 | 2/1980 | Japan | 324/228 |

OTHER PUBLICATIONS

"Improved Low Frequency Eddy Current Inspection for Cracks Under Installed Fasteners", Tech. Report AFWAL-TR-80-4150; Available from NTIS.

Primary Examiner—Gerard R. Strecker
Attorney, Agent, or Firm—Donald J. Singer; Bernard E. Franz

[57] ABSTRACT

An instrument having a multi-segmented cup core of a high permeability material with a center post. The outer wall of the cup contains equidistant holes and slots through which a plurality of individual windings are constructed to form a circular array of pick-up coils. A primary winding or search coil is constructed around the center post. Excitation of the search coil induces eddy currents in adjacent multi-layered bolt hole regions which in turn produce a voltage in each of the pick-up coils. As a crack in the material under test will cause an abnormal distribution of eddy currents, a comparison of the voltage measurements of the specimen under test with those of a reference sample will detect the presence of a crack and its corresponding orientation.

4 Claims, 8 Drawing Figures

EDDY CURRENT TEST PROBE WITH CIRCUMFERENTIAL SEGMENTS AND METHOD OF TESTING MATERIAL SURROUNDING FASTENER HOLES

RIGHTS OF THE GOVERNMENT

The invention described herein may be manufactured and used by or for the Government of the United States for all governmental purposes without the payment of any royalty.

BACKGROUND OF THE INVENTION

This invention relates to eddy current instruments for the non-destructive detection of flaws in electrically conductive articles and more particularly to the detection of flaws in the regions of electrically conductive material surrounding fastener holes.

Eddy current instruments of the type utilizing a source or exciting coil for inducing an alternating magnetic field in a material and a pick-up coil for detecting the magnetic field induced are widely used for locating flaws or imperfections in metallic materials. An eddy current instrument of this type detects a flaw by detecting the metal loss due to the flaw. The localized presence of a flaw or crack in the metal upsets the otherwise normal eddy current distribution. This abnormal apportionment of eddy current creates a resultant change in magnetic flux which is sensed by a change in the inductance of the pick-up coil.

Structural wing skins on cargo aircraft are spliced to each other in an overlapping configuration such that the skins are held together by means of fasteners mounted through holes in both skins. Fatigue damage can occur at the fastener hole in either layer of skin. Presently, two choices exist for the inspection of fastener holes in such structure. Either the fastener can be removed and the hole inspected with conventional eddy current techniques or shear wave ultrasonic methods can be utilized with the fastener intact. Neither choice is entirely satisfactory.

Conventional eddy current equipment is available with cup core type probes designed for the detection of large cracks emanating from fastener holes in second or interior layers. These existing probes interrogate the entire fastener hole during inspection and consequently are not very sensitive to the presence of small cracks. Large cracks can be detected without removing the fastener but detection of small cracks require removal of the fastener. If the structure to be tested has a large quantity of such fasteners, such as an aircraft's wings, the removal and re-installation of fasteners is costly and a potential source of structural damage. Ultrasonic shear wave inspection is an effective method of inspecting the faying surface region of the outer skin (layer) but it is considerably less effective in the region of a fastener hole countersink. When a faying surface sealant is present, the ultrasonic shear wave technique has the potential of penetrating into the inner layer, but the reduction to practice of this inner layer inspection has not occured. When this technique is developed, the faying surface side of the inner layer would not be as effectively inspected as the opposite side, and many structures exist that do not use sealants in a multi-layer configuration. Obviously, then, the requirement exists for an inspection technique that would complement the ultrasonic shear wave technique as well as not be dependent on the presence of sealant for inner layer inspections.

U.S. Pat. No. 3,166,710 to Schmidt discloses an apparatus including a segmented pick-up coil which is formed from a plurality of individual arcuate shaped coil segments disposed to form a single circular coil. This device is useful for detecting flaws in tubular structures such as a pipe, however, its applied magnetic field distribution renders the invention unsuitable for inspecting the wings of an aircraft.

SUMMARY OF THE INVENTION

An object of the invention is to provide an eddy current apparatus to inspect inner layers of overlapping structures for small cracks in bolt hole regions with the bolt or other fastener installed.

According to the invention, an eddy current probe is formed from a cup core which is divided into multiple arcuate segments, each segment having a pick-up coil wound about it. A center search coil, driven by an alternating current, is placed over a bolt hole with the fastener installed and induces eddy currents in the localized conductive region surrounding the bolt hole. By measuring the voltage in each pick-up coil and comparing the readings with a standard, an abnormal distribution of eddy current can be detected indicating the presence and orientation of a flaw in the region surrounding the bolt hole.

A feature of the invention relates to the provision that reveals segmented local variations in eddy currents rather than the integrated result of the entire distribution.

DETAILED DESCRIPTION OF THE INVENTION

A complete description of the invention, including design, analysis, fabrication techniques and operational implementation is contained in the technical report AFWAL-TR-80-4150, *Improved Low Frequency Eddy Current Inspection for Cracks under Installed Fasteners*, published by the Materials Laboratory, Air Force Wright Aeronautical Laboratories, Air Force Systems Command, Wright-Patterson Air Force Base, Ohio 45433 (available from National Technical Information Service (NTIS) under AD-A098 543/2). This report is hereby incorporated by reference.

Figure 1:
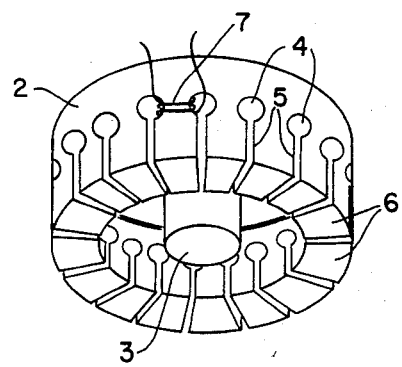
FIG. 1 is a pictorial view of a multi-segment coil that comprises the preferred embodiment.

As shown in FIG. 1, the preferred embodiment of the invention is composed of a cup core 2 with a center post 3, both of which are cylindrical in shape. The cup core contains a plurality of equidistant holes 4 each with a corresponding slot 5 so as to divide the cup core into segments 6. Many pick-up coils 7 of wire are wound between adjacent holes and about each segment such that each coil functions independently of the others. If a drive coil is wound around the center post, the probe can be used to detect small cracks in inner layers of conductive material by analyzing voltage readings from each pick-up coil.

Figure 2:
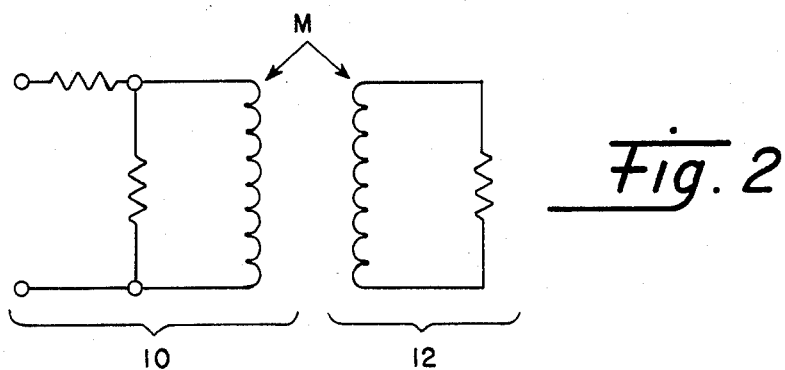
FIG. 2 is a schematic diagram of an equivalent circuit of a simple search coil.
Figure 3:
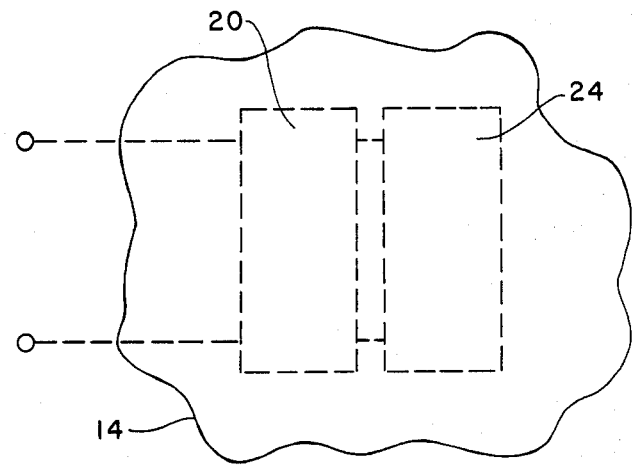
FIG. 3 is a drawing of the field volume about a coil coupled to a metal.

As shown in FIG. 2, the combination of a search coil and induced eddy current may be viewed as a transformer having a primary winding 10 equivalent to the search coil and a secondary winding 12 which is equivalent to the induced eddy current. The mutual inductance M is determined by the degree of coupling to the eddy current region and the properties of the material such as conductivity and permeability. If the coil is a one terminal pair, the input impedance of this circuit is determined by an integration of the fields within the whole volume 14 as shown in FIG. 3 in which a simple cup core 20 is placed adjacent to a conductive surface 24. The boundaries must extend to the region of zero field intensity. The lumped element equivalents of the coil are given by:

$$L = \frac{\mu}{I^2} \int B^2 \, dv$$

$$C = \frac{\epsilon}{V^2} \int E^2 \, dv$$

$$R = \frac{\sigma}{I^2} \int E^2 \, dv$$

where
L = inductance
C = capacitance
R = resistance
I = current
V = voltage
$\mu$ = permeability
$\epsilon$ = dielectric permittivity
$\sigma$ = conductivity
B = magnetic flux density
E = electric field If the crack occupies a small fraction of the total field volume, the change in eddy current distribution will be small and the resultant change in the coil impedance also small and difficult to measure. Since the simple terminal impedance is an integrated result, it is also influenced by non-flaw related effects. Such effects as coil lift off from surface, edge effects, and centering are not insignificant. This is particularly true in the case of inner layer cracks around bolt holes. When the cracked or flawed region is localized, it would be useful to have a probe that is sensitive to a local region yet also examines a larger area in a single probe placement. Such a probe is the multi-segment coil probe.

Figure 5:
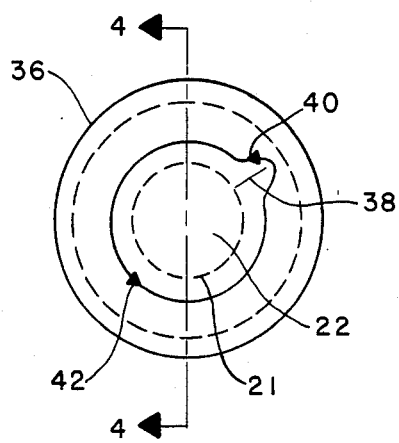
FIG. 5 is a top view of the cup core of FIG. 4.
Figure 4:
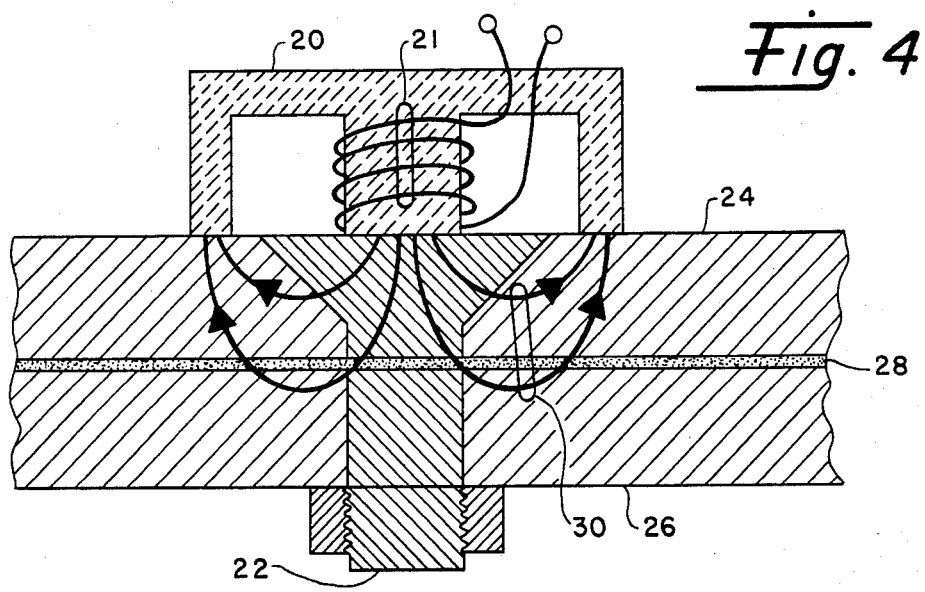
FIG. 4 is a cross-sectional view taken along lines 4—4 of FIG. 5 of a simple cup core coil coupled to a bolt hole having a fastener in place.

FIG. 4 shows a simple cup core 20 with a center wire winding 21 positioned over a bolt 22 which is connected to an outer layer 24 and an inner layer 26 of metal with a sealant 28 between the two. Flux lines 30 close in a cylindrically symmetric manner in the absence of any perturbing influence. FIG. 5 shows a top view of a cup with a bolt 22, a center winding 21, an outer rim 36 of the cup, and a crack 38 in the second layer material. The eddy current 40 in the region near the crack and the resultant flux will be disturbed locally while the eddy current 42 and flux in the other regions will be normal. The net flux change through the center core, which is effectively an integral of the outer rim flux, may not change significantly. By placing many sense coils in the outer rim of the cup core, the localized flux disturbances may be more readily determined. This multi-segment coil probe is created using a standard cup core that has been drilled and slotted as shown in FIG. 1.

Figure 6:
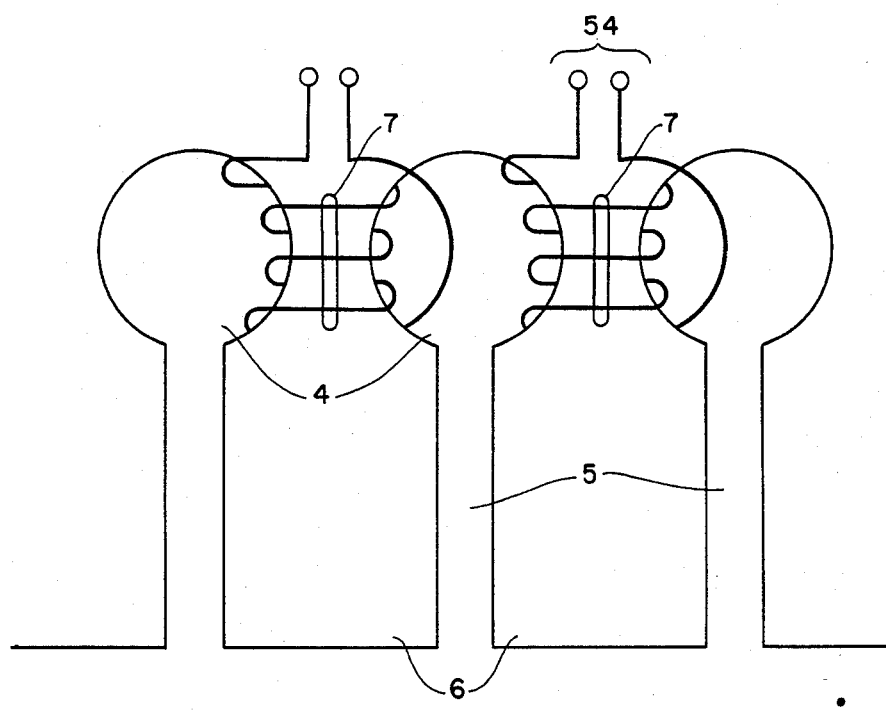
FIG. 6 is a side view of a segmented core.

FIG. 6 is a close-up view of the cup in FIG. 1 and shows the slots 5 and drilled holes 4 between the segments 6 as well as wire windings 7 between the holes. The segments and cup core can be constructed of any high permeability material, typically a ferrite substance. The hole allows space for the segment windings and the slots provide access for winding the coils as well as keeping the external flux separated until beyond the coils. Each wire winding is terminated with a pair of terminals 54 for measuring the voltage in each coil for each segment. The segment coil voltages are given by $$V_n = \frac{d\psi_n}{dt} = j\omega\psi_n$$

$$V_{n+1} = \frac{d\psi_{n+1}}{dt} = j\omega\psi_{n+1}$$

where
$\psi$ = magnetic flux
n = segment position

In this operating mode, each of the multi-segment coils really becomes another secondary winding when viewed in the framework of FIG. 2. The segment fluxes depend upon the reluctance of the path and determine the mutual inductances between the primary and various secondary windings. Thus, in the presence of a crack, the segment voltages near the flawed region would be different than those away from the region. The difference voltage, $$\Delta V_n = V_{n+1} - V_n$$

may be analyzed as a function of segment position or index, n, in order to determine the location and size of the flaw. Since the segment voltages are also a function of other parameters such as lift off and slight differences in segment coil construction, the actual implementation will require some form of reference measurement or signal analysis.

The preferred usage mode for the multi-segment probe is to drive the center coil with an alternating current at the frequency of interest and measure the open circuit voltages at the segments. If these voltages are then recorded for a specimen without flaws and used as a reference for a flawed specimen, the difference may be used to determine the presence of a flaw. The difference voltage is given by:

$$V_{fn} = V_n^\circ - V_n$$

where $V_n^\circ$ is the reference voltage measured without the flaw and $V_n$ is the segment voltage with the flaw. By comparing the segment variations of $V_{fn}$ the flaw location may be determined.

Four effects may significantly alter this simple picture; centering, geometrical distortion in the hole, lift off, and edge effects. First, if the coil is not centered over the flawed specimen the same as for the reference specimen, the off centering itself will cause variations in $V_{fn}$ between various segments. However, the center coil, when operated as a normal one terminal pair search coil at higher frequencies, can be used to center the coil over the bolt hole. Any slight off centering or geometrical distortions would result in gradual variations of the segment voltage as a function of position around the circumference. Similarly, lift off would also slow variations of the segment voltages. However, a localized flaw, or any first layer crack, would produce more immediate effects in that segment nearest the flaw. Therefore, an examination of the rate of change of the voltage $V_{fn}$ as a function of segment position is used to separate the flaw effects from other effects.

Figure 7:
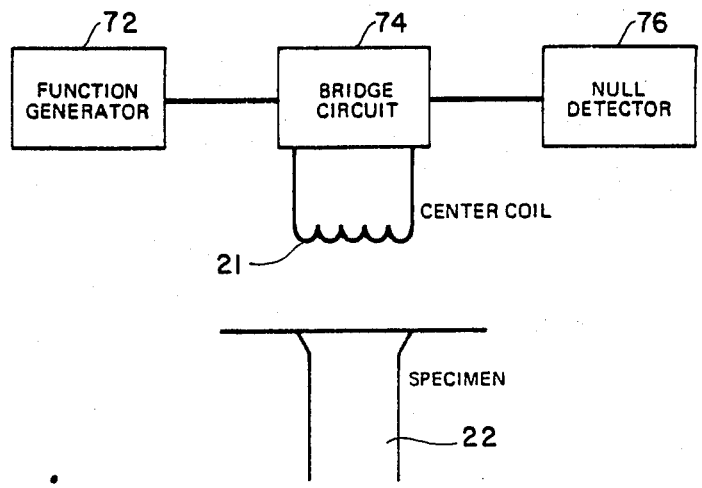
FIGS. 7 and 8 are block diagrams showing a method of centering.
Figure 8:
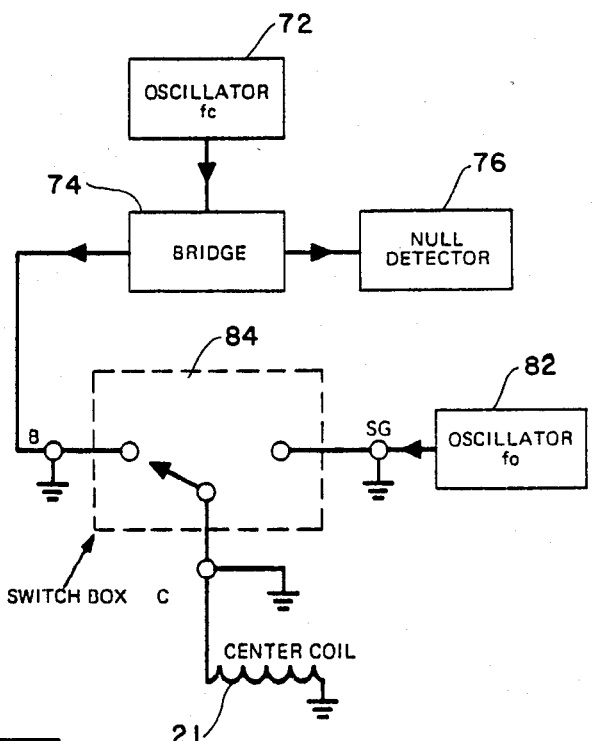

Centering of the bolt hole was accomplished, as shown in FIG. 7, by a Maxwell bridge circuit 74, a null detector 76, and a second function generator 72 operated at 20 KHz. The same center driving coil 21 used for crack detection was used for centering purposes. If the probe was centered over the fastened hole, the bridge would be in a balanced state, and the null detector would show no error voltage due to the symmetrical geometry of the fastener head. If the probe was off center, it would cause the bridge to unbalance and would be indicated by the null detector. FIG. 8 shows the schematic of a mechanical switch box layout. The box 84 switches between centering frequency, $f_c$ from oscillator 72, and normal detecting operating frequency, $f_0$ from oscillator 82. This set-up enabled the multisegment probe to be used as both a centering and a detecting device without any cable connect and disconnect required.

In the case of second-surface crack detection in bolt holes with fasteners in place, the flaw-induced field changes are much smaller due to shielding by the first layer and the distance between crack and segments. In order to probe into the second layer region, lower frequencies must be employed. However, the lower frequency eddy currents also spread laterally and make the probe sensitive to the panel edges and adjacent bolt holes. The coil frequency is thus a critical parameter and must be chosen, if possible, to optimize the second layer crack detection. Operation between 3000 Hz and 700 Hz was found satisfactory. Four hundred Hz was chosen because overall it seemed to give the best signal to noise ratio and the sharpest crack slope indication. Again it is important to destinguish the more rapid field variations caused by edge effects. But when the flaw signals are as small as those caused by coil placement errors, it may be necessary to perform the segment calibrations in place rather than on a separate reference specimen and then transferring to the specimen of interest. This procedure is required when the error voltage caused by inaccuracies in coil placement exceeds the voltage change due to the flaw itself. In-place calibration may be accomplished by operating the coil at a high frequency where the flaw and panel edge regions are cut off due to skin effects. The variations between segment voltages may be accounted for as follows. In general the segment voltages may be written as:

$$V_n = V_n^\circ + \Delta V_{no} + \Delta V_{nF}$$

where $V_n^\circ$ is the segment voltage with no flaw or alignment errors, $\Delta V_{no}$ is the error voltage due to alignment and coil fabrication variations, and $\Delta V_{nF}$ is the change due to the flaw and any other low frequency effect such as edges. At a high frequency where the flaw and edges are cutoff by skin effect, $$V_n(\text{fh}) = V_n^\circ(\text{fh}) + \Delta V_{no}(\text{fh})$$

At any other frequency, the voltage is just a constant multiple of $V_n(\text{fh})$.

$$V_n(f) = K V_n(\text{fh})$$

In other words, the ratios of segment voltages are assumed independent of frequency if the flaw or edge effects are not present. The dependence of K on frequency may be determined by measurements made on a carefully aligned reference sample. In the presence of a second-surface crack measured at a lower frequency, $$V_n(\text{fl}) = K V_n(\text{fn}) + \Delta V_{nF}$$

or $$\Delta V_{nF} = V_n(\text{fl}) - K V_n(\text{fh})$$

The importance of the above procedure is that all of the right hand side of the above equation is measured within the same coil placement. Determining what part of the $\Delta V_{nF}$ is due to the flaw, as opposed to an edge effect, will require an analysis of the rate of voltage change with respect to segment position. Since the edge effects are more diffuse, the segment-to-segment variations should be smaller even though $\Delta V_{nF}$ might be largely caused by the edge effect. In this case the second surface crack should appear as a small segment-to-segment variation on top of the edge effect. The nature of the edge effect could be obtained by measurements made upon a reference sample as a function of frequency and compared to the case of a second surface crack.

Operationally, measurements of open circuit voltages are obtained for each segment and compared with corresponding measurements made with a flawless reference sample. A discrepency in the comparable measurements indicates the presence of a crack or other localized flaw and the identification of the segment determines the flaw orientation. These voltages measurements can be performed in any variety of acceptable methods. For a recommended method involving a minicomputer, consult the previously mentioned technical report.

Manufacturing and fabrication techniques are also contained in the same report.

CONCLUSIONS

The program objective was to develop a low-frequency eddy current technique to inspect inner layers of aluminum structure for cracking in holes with the fastener installed. The detection goals were 0.1-inch radial depth through-the-thickness crack in the inner layer, under a 0.25-inch thick outer layer with the titanium fastered installed.

The program objective has been obtained and fully demonstrated. It was gratifying to discover the great sensitivity of the array probe to detect second layer notches as small as 0.04 inch through 0.25 inch in the first layer.

The unique features of this array probe for application to second layer cracks in bolt holes are:

1. The probe reveals the local variations in eddy currents rather than the integrated result of the entire distribution; therefore, the flaw orientatin can be determined.

2. The circumference of the hole is scanned electronically rather than mechanically. This feature significantly reduces errors due to liftoff and centering.

3. Electronic centering is achieved with the same probe.

4. Inspection of the holes is accomplished with the fasteners in-place.

5. The probe is not affected adversely by the sealant material used between the layers being held together by the fastener.

Thus, while preferred constructional features of the invention are embodied in the structure illustrated herein, it is to be understood that changes and variations may be made by the skilled in the art without departing from the spirit and scope of the invention.

I claim:

1. A method of testing specimens with fastener holes in multi-layer material which may have sealant material between layers using an instrument comprising a cup core formed of high permeability material having an outer cylindrical wall and an inner center post with the outer wall being joined to the center post at one end and the other end terminating with a rim so as to form an open end of a cup, the outer wall containing a plurality of equidistant openings extending completely through the outer wall, and along the cylindrical length from the rim to a plane perpendicular to the cylindrical axis through the outer wall, to thereby provide a plurality of segments in the form of peripheral posts around the outer wall, with a plurality of segments in each quadrant, with the segments having planes of symmetry through the cylindrical axis which have equal angles between them completely around the cylinder, there being a search coil wound around said center post, and a pick-up coil wound around each segment, the pick-up coils being substantially the same size and shape, at substantially the same location on the respective segments;

said method comprising the steps of:
exciting the center post winding with alternating current of a selected operating frequency;
scanning the pick-up coils and measuring the voltage of each individual pick-up coil with the instrument centered on a fastener of a flawless reference specimen;
scanning the pick-up coils and measuring the voltage of each individual pick-up coil with the instrument centered on a fastener of a specimen to be tested with the same excitation voltage; and
comparing the voltage of each individual pick-up coil with the corresponding voltage from the reference specimen whereby flaws in the specimen being tested are indicated by discrepencies between the two voltage readings and flaw orientation is determined by identification of the segment coil;
said frequency being lowered for testing deeper layers of material.

2. The method according to claim 1, wherein the instrument has sixteen of said segments, and the frequency for testing deeper layers of material is approximately 400 Hertz.

3. The method according to claim 1, wherein the instrument is centered on a fastener of a specimen by connecting the center post winding to a bridge circuit, the bridge circuit being also connected to a null detector, exciting the center post winding via the bridge circuit with a voltage at a centering frequency which is substantially higher than said operating frequency, flaw and other effects being cutoff due to skin effects at the centering frequency, and positioning the instrument so that the bridge is balanced with no error voltage indicated by the null detector.

4. A method of testing specimens with fastener holes in multilayer material which may have sealant material between layers using an instrument comprising a cup core formed of high permeability material having an outer cylindrical wall and an inner center post with the outer wall being joined to the center post at one end and the other end terminating with a rim so as to form an open end of a cup, the outer wall containing a plurality of equidistant openings extending completely through the outer wall, and along the cylindrical length from the rim to a plane perpendicular to the cylindrical axis through the outer wall, to thereby provide a plurality of segments in the form of peripheral posts around the outer wall, with a plurality of segments in each quadrant, with the segments having planes of symmetry through the cylindrical axis which have equal angles between them completely around the cylinder, there being a search coil wound around said center post, and a pick-up coil wound around each segment, the pick-up coils being substantially the same size and shape, at substantially the same location on the respective segments;

said method comprising the steps of:
centering the instrument on a fastener of a specimen to be tested by connecting the center post winding to a bridge circuit, the bridge circuit being also connected to a null detector, exciting the center post winding via the bridge circuit with a voltage at a very high centering frequency, and positioning the instrument so that the bridge is balanced with no error voltage indicated by the null detector;
exciting the center post winding with alternating current of a selected relatively high frequency;
measuring the voltage of each individual pick-up coil
exciting the center post winding with alternating current of a selected lower operating frequency;
scanning the pick-up coils and measuring the voltage of each individual pick-up coil
comparing the voltage of each individual pick-up coil as measured with the lower operating frequency with the corresponding voltage as measured with said relatively high frequency, the two sets of voltages being measured with the same instrument placement, whereby flaws in the specimen being tested are indicated by discrepencies between the two voltage readings and flaw orientation is determined by identification of the segment coil;
said lowered operating frequency being lowered further for testing deeper layers of material.

* * * * *